US012702283B2

(12) United States Patent
Suzuki et al.

(10) Patent No.: US 12,702,283 B2
(45) Date of Patent: Aug. 11, 2026

(54) MEDICAL INSERTION EQUIPMENT SYSTEM, CAPSULE, AND MEDICAL INSERTION EQUIPMENT DISINFECTION METHOD

(71) Applicant: OLYMPUS MEDICAL SYSTEMS CORP., Tokyo (JP)

(72) Inventors: Takeo Suzuki, Hachioji (JP); Keita Ozawa, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 595 days.

(21) Appl. No.: 18/126,810

(22) Filed: Mar. 27, 2023

(65) Prior Publication Data

US 2023/0309807 A1 Oct. 5, 2023

Related U.S. Application Data

(60) Provisional application No. 63/325,255, filed on Mar. 30, 2022.

(51) Int. Cl.
*A61B 1/12* (2006.01)
*A61L 2/26* (2006.01)
*A61L 103/15* (2026.01)

(52) U.S. Cl.
CPC ................ *A61B 1/126* (2013.01); *A61L 2/26* (2013.01); *A61L 2103/15* (2026.01)

(58) Field of Classification Search
CPC ..... A61B 1/041; A61B 1/00137; A61B 1/121; A61B 1/122; A61B 1/123; A61B 1/125;
(Continued)

(56) References Cited

U.S. PATENT DOCUMENTS 4,627,850 A * 12/1986 Deters .................. A61K 9/0004 428/318.6
5,860,916 A * 1/1999 Pylant ................. A61M 3/0279 600/114

(Continued)

FOREIGN PATENT DOCUMENTS

CN 101184431 A 5/2008
CN 101209197 A 7/2008

(Continued)

OTHER PUBLICATIONS

Office Action dated Apr. 22. 2026, issued in corresponding Chinese Patent Application No. 202310316167.8.

*Primary Examiner* — Ryan N Henderson
(74) *Attorney, Agent, or Firm* — Morgan, Lewis & Bockius LLP

(57) ABSTRACT

A medical insertion equipment system comprises a capsule including an outer shell and an interior space, a disinfectant that is located in the interior space of the capsule, and a medical insertion instrument that includes an operation section, an insertion section configured for insertion into a subject, an insertion conduit located in the insertion section, and a fixture located in the operation section, the fixture including a body having a receiver space for holding at least a portion of the capsule, and wherein the insertion conduit extends along an insertion axis from a distal end side of the insertion section to a proximal end side of the insertion section, and wherein the fixture includes an opening in a surface of the receiver space, and wherein the opening is in fluid communication with the insertion conduit via a connecting conduit.

18 Claims, 17 Drawing Sheets

(58) Field of Classification Search
CPC ..... A61B 1/126; A61B 1/015; A61L 2202/24; A61L 2/00; A61L 2/26; A61L 2013/15
See application file for complete search history.

(56) References Cited

U.S. PATENT DOCUMENTS 5,902,547 A 5/1999 Hill
D452,004 S * 12/2001 Baker .......................... D24/135
2003/0013938 A1* 1/2003 Iddan ..................... A61B 1/041 600/129
2003/0139647 A1* 7/2003 Raz .................... A61B 1/00147 600/104
2006/0200176 A1* 9/2006 Matsuno ............ A61B 1/00089 606/140
2007/0049796 A1* 3/2007 Fujikura ............ A61B 1/00101 600/116
2007/0225552 A1* 9/2007 Segawa .............. A61B 1/00144 600/102
2008/0015413 A1* 1/2008 Barlow .............. A61B 1/00147 600/114
2008/0319785 A1 12/2008 Moriyama
2009/0081767 A1 3/2009 Ogawa et al.
2009/0090398 A1 4/2009 Onishi
2009/0253999 A1* 10/2009 Aoki .................. A61B 1/00158 600/565
2012/0071710 A1* 3/2012 Gazdzinski .............. A61B 8/12 600/101
2012/0101331 A1* 4/2012 Gilad ................. A61B 1/00147 600/114
2016/0227988 A1* 8/2016 Jiang .................. A61B 1/00101
2024/0198066 A1* 6/2024 Schoellhammer ..... A61B 5/073

FOREIGN PATENT DOCUMENTS

CN 209934627 U 1/2020
JP 3040613 U 8/1997
JP H10-262910 A 10/1998
JP 2004-194976 A 7/2004
JP 2006-087520 A 4/2006
JP 2006-260261 A 9/2006

* cited by examiner

MEDICAL INSERTION EQUIPMENT SYSTEM, CAPSULE, AND MEDICAL INSERTION EQUIPMENT DISINFECTION METHOD

RELATED APPLICATION DATA

This application is based on and claims priority under 35 U.S.C. § 119 to U.S. Provisional Application No. 63/325,255 filed on Mar. 30, 2022, the entire contents of which are incorporated herein by reference.

BACKGROUND

1. Field of the Disclosure

The present disclosure relates to an insertion equipment system, a capsule, and a medical insertion equipment disinfection method conforming to medical insertion equipment including a conduit on an inside of an insertion section.

2. Description of the Related Art

Conventionally, insertion equipment functioning as a medical apparatus has been widely used in a medical field. A primary example of such insertion equipment is an endoscope. The endoscope can perform, by inserting an elongated insertion section into a subject, observation, treatment, and the like for a site to be examined. In general, the treatment for the site to be examined is performed by inserting various treatment instruments through a treatment instrument channel provided in the insertion section.

As a medical appliance such as a treatment instrument used for various treatments for which an endoscope is used, a single-use (disposable) medical appliance has been widely adopted. Sterilization treatment is applied to such a single-use medical appliance in a factory or the like at a manufacturing source. The medical appliance after the sterilization treatment is delivered to a hospital or the like at a request source in a state in which the medical appliance is sealed by a package for sterilization. Further, in recent years, single-use has been advanced for the endoscope itself as well.

SUMMARY

A medical insertion equipment system according to an aspect of the present disclosure includes: a capsule including an outer shell and an interior space, a disinfectant is located in the interior space of the capsule; and a medical insertion instrument including: an operation section, an insertion section configured for insertion into a subject, an insertion conduit located in the insertion section, and a fixture located in the operation section, the fixture including a body having a receiver space for holding at least a portion of the capsule, wherein the insertion conduit extends along an insertion axis from a distal end side of the insertion section to a proximal end side of the insertion section, wherein the fixture includes an opening in a surface of the receiver space, and wherein the opening is in fluid communication with the insertion conduit via a connecting conduit.

A capsule according to an aspect of the present disclosure includes: an outer shell having a groove on an inside surface or on an exterior surface and a disinfectant located in an interior space formed by the outer shell, wherein a rupture strength of a section of the outer shell at which the groove is located is less than a rupture strength of the outer shell where the groove is not located.

A medical insertion equipment disinfection method according to an aspect of the present disclosure includes: holding, on an end portion side of a conduit of insertion equipment on an outside of a subject, the insertion equipment including an insertion section that is inserted into an inside of the subject and a conduit provided in the insertion section and configured to cause the inside and the outside of the subject to communicate with each other, a capsule including an outer shell including a space on an inside and a disinfectant stored in the space in the outer shell, inserting a treatment instrument from an end portion side of the conduit on the outside of the subject and breaking the outer shell of the capsule with the treatment instrument inserted into the conduit to leak the disinfectant to an inside of the conduit.

DETAILED DESCRIPTION

In general, a single-use specification endoscope can be directly used for treatments of various operative procedures without performing sterilization treatment and the like after being taken out from a sterilization package. On the other hand, even the single-use specification endoscope is exposed to environmental bacteria such as falling bacteria and floating bacteria in air before a treatment is started after the endoscope is taken out from the sterilization package.

According to embodiments explained below, it is possible to reduce influence of environmental bacteria on a subject.

Figure 1:
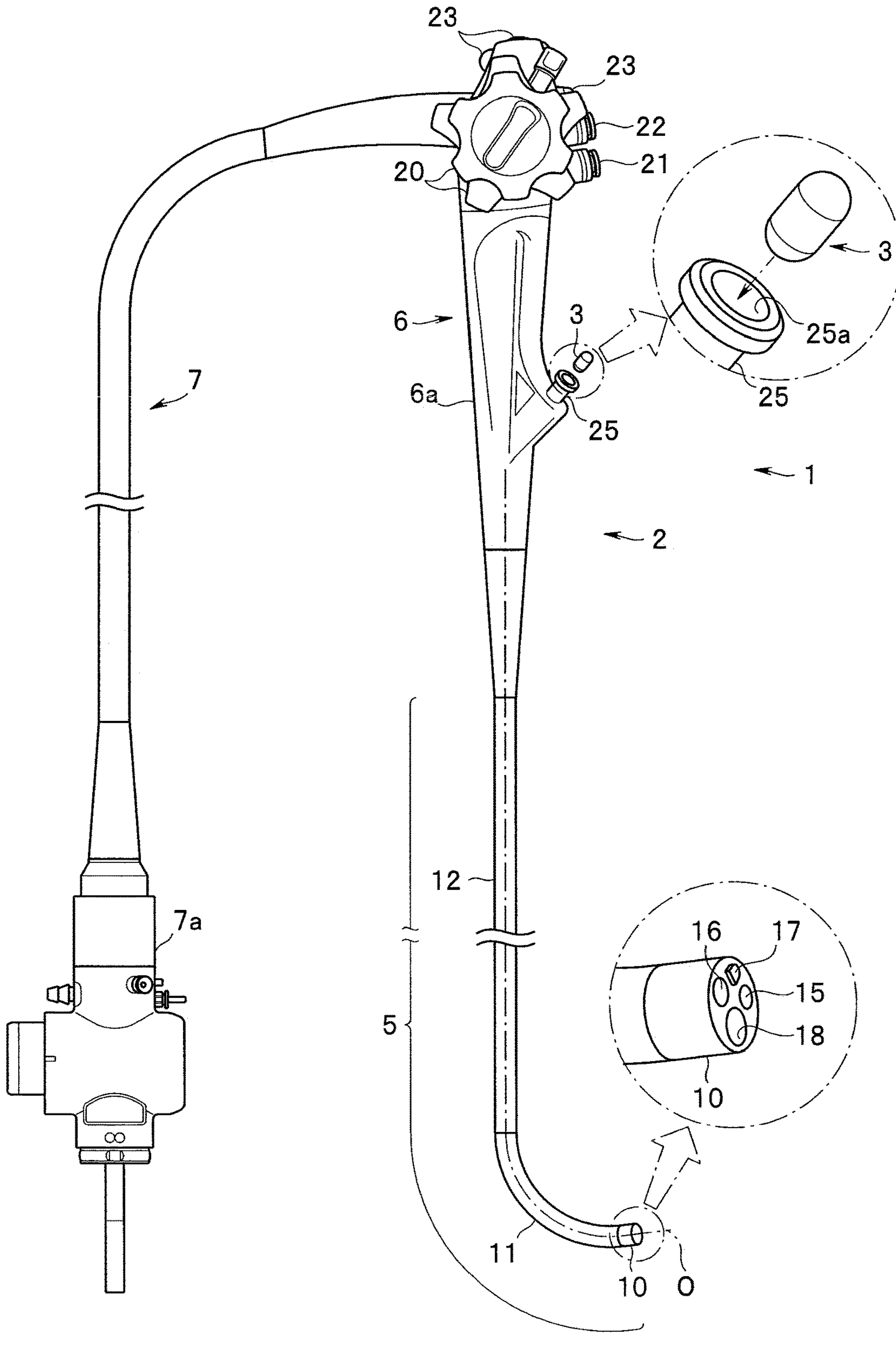
FIG. 1 relates to a first embodiment and is a schematic configuration diagram of an endoscope system.

Embodiments of the present disclosure are explained below with reference to the drawings. FIG. 1 to FIG. 4 relate to a first embodiment of the present disclosure and FIG. 1 is a schematic configuration diagram of an endoscope system serving as an example of a system of medical insertion equipment (medical insertion instrument). Note that, in the figures used for the following explanation, scales are differentiated for each of components in order to show the respective components in recognizable sizes on the drawings. Therefore, the present disclosure is not limited to only quantities of the components, shapes of the components, ratios of the sizes of the components, and relative positional relations among the respective components described in the drawings.

An endoscope system 1 shown in FIG. 1 includes an endoscope 2 and a capsule 3 used in the endoscope 2.

The endoscope 2 is, for example, a single-use endoscope that is discarded after being used only once. The endoscope 2 includes an insertion section 5, an operation section 6, and a universal cable 7.

The insertion section 5 includes a distal end portion 10, a bending section 11, and a flexible tube section 12. The distal end portion 10, the bending section 11, and the flexible tube section 12 are provided in order from a distal end side along an insertion axis O extending from the distal end side toward a proximal end side of the insertion section 5.

The distal end portion 10 includes, for example, an illumination optical system 15, an image pickup unit 16, a nozzle 17, and a distal end side opening 18 functioning as an opening section.

The illumination optical system 15 forms an illumination window on a distal end face of the distal end portion 10. For example, the illumination optical system 15 irradiates a subject with illumination light transmitted from a not-shown light source apparatus through a light guide.

The image pickup unit 16 includes an image pickup optical system and an image pickup device. An image pickup optical system forms an observation window on the distal end face of the distal end portion 10. The image pickup optical system forms, as an optical image, reflected light from the subject irradiated with the illumination light. The image pickup device picks up the optical image formed by the image pickup optical system and generates an image pickup signal. The image pickup device is, for example, an image sensor. The image pickup signal generated by the image pickup device is outputted through a signal cable connected to the image pickup unit.

The nozzle 17 is connected to a gas feeding and liquid feeding channel (not shown) inserted through the insertion section 5. A distal end of the nozzle 17 is directed to an objective lens (the observation window) provided at a distal end of the image pickup optical system. Consequently, the nozzle 17 is capable of jetting, to the objective lens, gas or liquid supplied from the gas feeding and liquid feeding channel.

The distal end side opening 18 is connected to a distal end of a treatment instrument channel 19 (see FIGS. 2 and 3) functioning as a conduit provided on an inside of the insertion section 5. The distal end side opening 18 is an opening for projecting, to an outside of the distal end portion 10, a distal end side of a treatment instrument (not shown) inserted into the treatment instrument channel 19. Consequently, a surgeon or the like is capable of performing various treatments for the subject.

Note that the treatment instrument channel 19 in the present embodiment also includes a function of a suction conduit for suctioning a suction target object such as body fluid, cleaning liquid, and a biological tissue from the subject. Therefore, the distal end side opening 18 also includes a function of a suction port.

For example, the bending section 11 is configured to be bendable in upward, downward, left, and right four directions. When the bending section 11 is bent, a direction of the distal end portion 10 changes. Consequently, an observation direction by the image pickup unit 16 changes. The bending section 11 is also bent to improve insertability of the insertion section 5 in the subject. Note that, here, an example is explained in which the bending section 11 is configured to be bendable in the four directions. However, the bending section 11 may be configured to be bendable in two directions. The endoscope 2 may be a type not including the bending section 11.

The flexible tube section 12 is a flexible tube section capable of bending according to a shape of a subject into which the insertion section 5 is inserted. Here, a flexible endoscope including the flexible tube section 12 is explained as an example of the endoscope 2. However, the endoscope 2 may be a rigid endoscope including a rigid tube section.

The operation section 6 is continuously provided on a proximal end side of the insertion section 5. The operation section 6 includes a grasping section 6*a* that the surgeon or the like is capable of grasping with a hand.

The operation section 6 includes, further on the proximal end side than the grasping section 6*a*, a bending operation lever 20, a gas feeding and liquid feeding button 21, a suction button 22, and a plurality of button switches 23.

The bending operation lever 20 is an operation member for bending the bending section 11.

The gas feeding and liquid feeding button 21 is an operation button for feeding gas or liquid from the nozzle 17 to the objective lens of the image pickup unit 16.

The suction button 22 is an operation button for suctioning a suction target object from the distal end side opening 18 provided at the distal end portion 10 through the treatment instrument channel 19.

Operation for executing various functions of the endoscope 2 can be optionally allocated to the button switches 23. For example, operation related to an image pickup function can be allocated to the button switches 23.

The operation section 6 includes a pipe sleeve 25 (fixture) for treatment instrument insertion further on the distal end side than the grasping section 6*a*. The pipe sleeve 25 is connected to the treatment instrument channel 19 via a relay tube 26 (connecting conduit) on an inside of the operation section 6 (see FIGS. 2 and 3). In other words, the pipe sleeve 25 provided in the operation section 6 is connected to an end portion side (the proximal end side) of the treatment instrument channel 19 on an outside of the subject via the relay tube 26.

Figure 2:
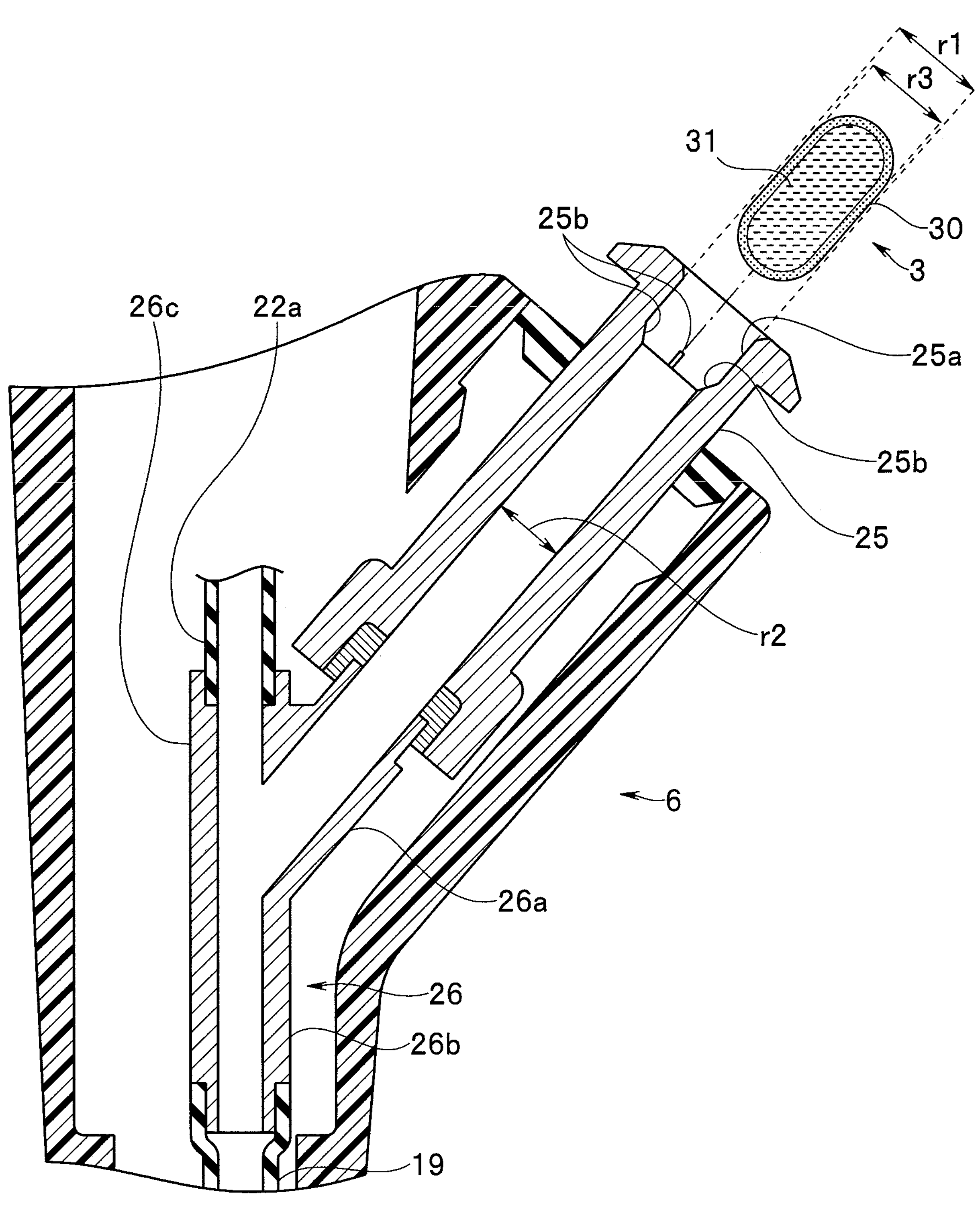
FIG. 2 relates to the first embodiment and is a main part sectional view showing an operation section and a capsule.
Figure 3:
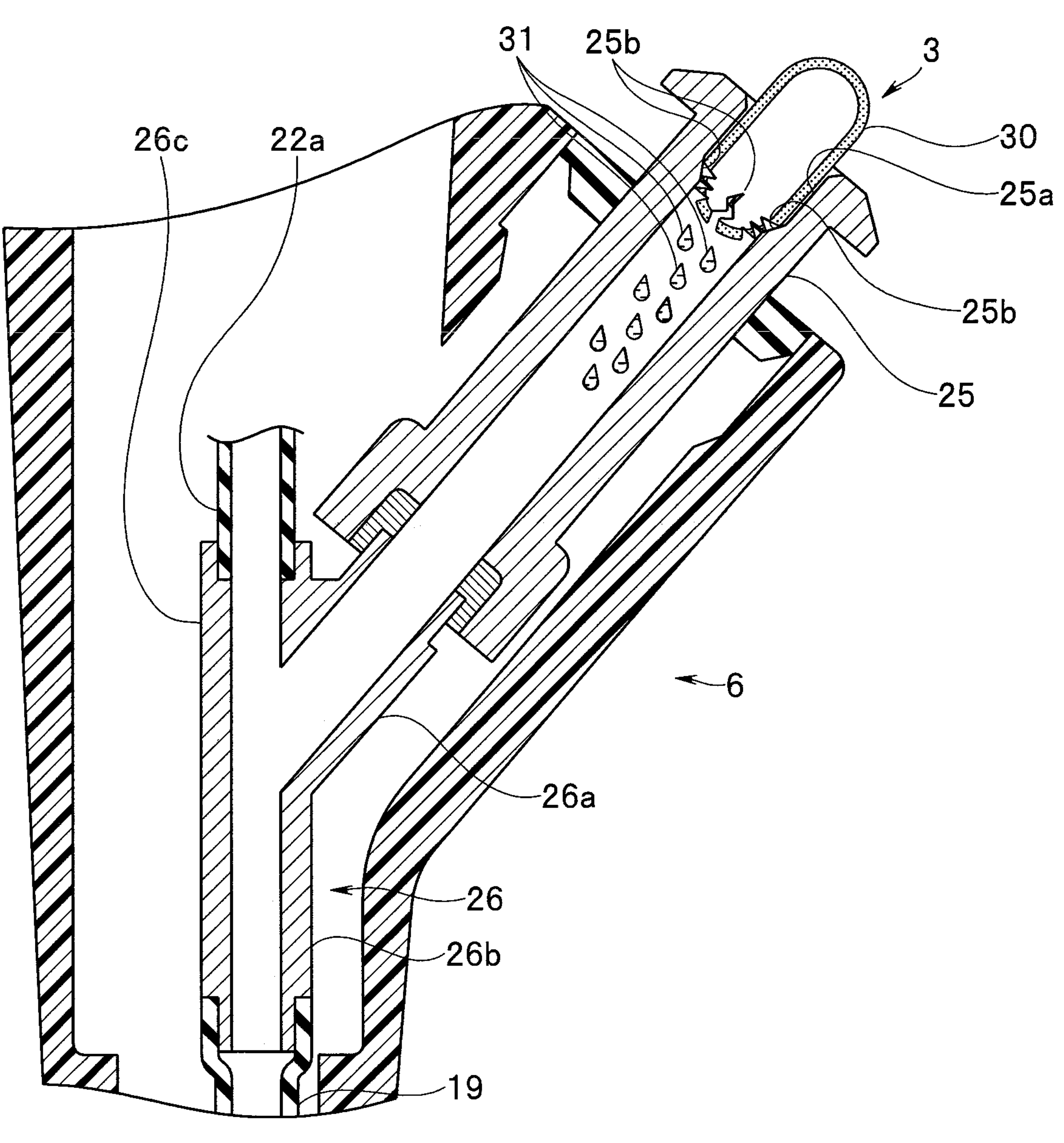
FIG. 3 relates to the first embodiment and is a main part sectional view showing the operation section and a broken capsule.

Note that, for example, as shown in FIGS. 2 and 3, the relay tube 26 is configured by, for example, a branch tube formed in a trifurcate structure. In other words, the relay tube 26 includes a first branch tube 26*a* connected to the pipe sleeve 25, a second branch tube 26*b* connected to the treatment instrument channel 19, and a third branch tube 26*c* connected to the suction button 22 via a suction tube 22*a*.

Consequently, the surgeon or the like is capable of inserting various treatment instruments into an inside of the treatment instrument channel 19 from the pipe sleeve 25. The surgeon or the like is also capable of suctioning body fluid and the like via the treatment instrument channel 19 by operating the suction button 22.

A holding section 25*a* (receiver) for holding the capsule 3 is formed on an inside of the pipe sleeve 25. The holding section 25*a* is formed by, for example, setting an inner diameter r1 near an opening end portion on the proximal end side of the pipe sleeve 25 larger than an inner diameter r2 on the distal end side of the pipe sleeve 25. Consequently, the holding section 25*a* is capable of holding the capsule 3 on the end portion side of the treatment instrument channel 19 on the outside of the subject.

Figure 4:
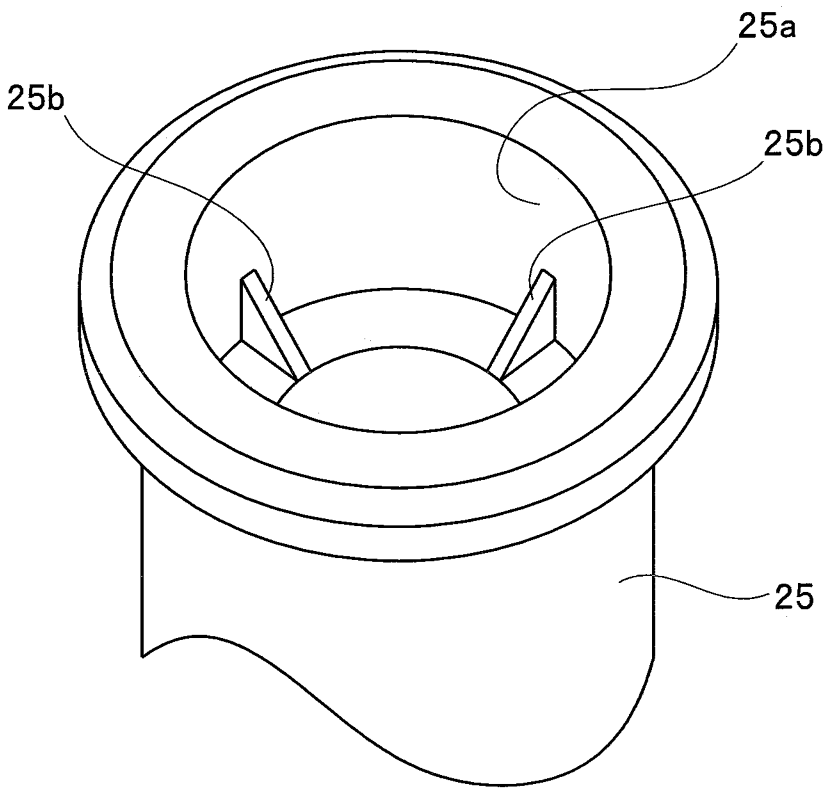
FIG. 4 relates to the first embodiment and is a perspective view of a pipe sleeve.

Further, a plurality of protrusions 25*b* are provided on an inside of the holding section 25*a* (see FIG. 2 to FIG. 4). The protrusions 25*b* are set in positions where the protrusions 25*b* are in contact with the capsule 3 when the capsule 3 is inserted into the inside of the holding section 25*a*. In other words, the pipe sleeve 25 may have a closed receiver that is sized to contain the capsule 3.

For example, the universal cable 7 is extended from the proximal end side of the operation section 6. The universal cable 7 is a connection cable for connecting the endoscope 2 to a light source apparatus, a processor, a liquid feeding tank, a suction pump, and the like (all of which are not shown). Therefore, the light guide, the signal cable, the gas feeding and liquid feeding channel, the suction channel, and the like explained above are inserted through an inside of the universal cable 7.

An endoscope connector 7*a* is provided at an extension end of the universal cable 7. The endoscope connector 7*a* is connectable to, for example, various kinds of equipment such as the light source apparatus including a gas feeding pump, the processor, the liquid feeding tank, and the suction pump (all of which are not shown).

Note that, when the endoscope 2 in the present embodiment is single-use specification, after sterilization treatment is applied to the endoscope 2, the endoscope 2 is shipped in a state in which the endoscope 2 is sealed by a sterilization package. Therefore, the endoscope 2 is maintained in a sterilized state until the endoscope 2 is taken out from the sterilization package.

Figure 5:
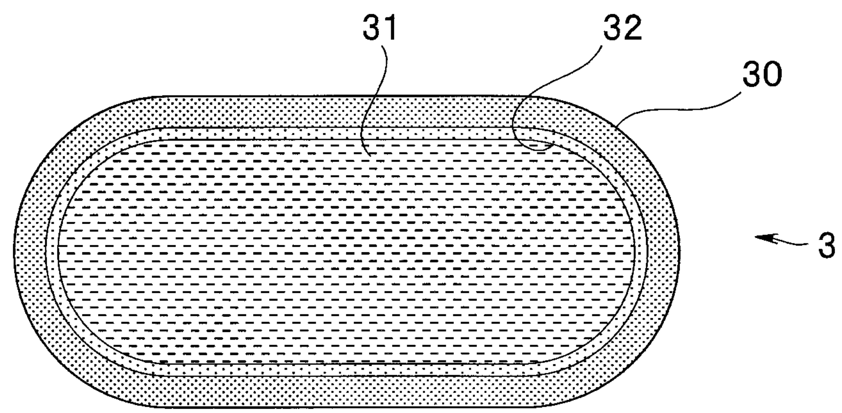
FIG. 5 relates to the first embodiment and is a sectional view of the capsule.

As shown in FIGS. 2 and 5, the capsule 3 includes an outer shell 30 and a disinfection solution 31 functioning as a disinfectant.

The outer shell 30 is formed in, for example, a substantially long spherical shape. The outer shell 30 includes a closed space on an inside.

The outer shell 30 is formed by, for example, gelatin, starch, agar, or cellulose (hereinafter collectively referred to as gelatin or the like). Here, the gelatin or the like forming the outer shell 30 is harmless to a human body. The gelatin or the like forming the outer shell 30 contains a material that is melted by at least one of body fluid or body temperature of the human body. The gelatin or the like forming the outer shell 30 may have a melting temperature between 34° C. and 38° C. It may be preferably the melting temperature is between 35° C. and 38° C. The gelatin or the like forming the outer shell 30 may include a material that is melted by blood, urine, saliva, secretions from an esophagus, gastric juice, intestinal juice, bile, pancreatic juice, or other digestive fluid.

Since a material such as gelatin is used, the outer shell 30 has resistance (chemical resistance) to ethanol and the like.

Note that, depending on a type of the disinfection solution 31, a protective film 32 having chemical resistance to the disinfection solution may be formed on an inner circumferential surface of the outer shell 30. For example, it is also possible to form the outer shell 30 of the capsule 3 with starch and form the protective film 32 using gelatin on the inner circumferential surface of the outer shell 30.

An outer diameter r3 in a direction orthogonal to a longitudinal direction of the outer shell 30 is set to be larger than the inner diameter r2 on the distal end side of the pipe sleeve 25 and smaller than the inner diameter r1 on the proximal end side of the pipe sleeve 25. In other words, the outer diameter r3 of the outer shell 30 is set to be larger than an inner diameter R2 of the pipe sleeve 25 further on the distal end side than the holding section 25*a* (and an inner diameter of the treatment instrument channel 19) and smaller than an inner diameter of the holding section 25*a*. Since the outer shell 30 is formed in such dimensions, basically, the outer shell 30 does not move to the distal end side on the inside of the pipe sleeve 25 and is held on the inside of the holding section 25*a*.

It is possible to easily break the outer shell 30 formed in this way when predetermined stress is applied to the outer shell 30. For example, it is possible to easily break the outer shell 30 with the protrusions 25*b* by applying stress to, from an outside of the pipe sleeve 25, the outer shell 30 held by the holding section 25*a*.

As the disinfection solution 31, for example, alcohol (ethanol, isopropanol, or the like), a hydrogen peroxide solution (oxydol), or sodium hypochlorite is suitably used. Such a disinfection solution 31 is diluted to concentration less harmful to a human body and used.

The disinfection solution 31 is encapsulated (stored) in an internal space of the outer shell 30. The outer shell 30 is broken, whereby the disinfection solution 31 is capable of leaking from the inside to the outside of the outer shell 30.

Here, an amount of the disinfection solution 31 encapsulated in the outer shell 30 may be, for example, at least an amount capable of spreading the disinfection solution 31 to entire circumferences of inner wall surfaces of the pipe sleeve 25 and the treatment instrument channel 19 in a range from the pipe sleeve 25 to a predetermined part of the treatment instrument channel 19. In addition, the amount of the disinfection solution 31 encapsulated in the outer shell 30 may be, for example, an amount with which the disinfection solution 31 does not reach the distal end side opening 18 of the treatment instrument channel 19 when the disinfection solution 31 is caused to flow in from the proximal end side. Note that the predetermined part of the treatment instrument channel 19 is a part that environmental bacteria intruding from the pipe sleeve 25 can reach.

The capsule 3 configured in this way is inserted into the inside of the pipe sleeve 25 from an end portion of the pipe sleeve 25 on the outside of the subject (see FIG. 2). Consequently, the capsule 3 is held by the holding section 25*a* formed at a proximal end portion of the pipe sleeve 25.

Note that the insertion of the capsule 3 into the pipe sleeve 25 can be performed at any timing after the endoscope 2 is taken out from the sterilization package. For example, the insertion of the capsule 3 into the pipe sleeve 25 can be performed at timing immediately before the insertion section 5 is inserted into the subject. Alternatively, the insertion of the capsule 3 into the pipe sleeve 25 can be performed at timing after the insertion section 5 is inserted into the subject and timing immediately before the treatment instrument is inserted into the inside of the treatment instrument channel 19.

The capsule 3 is pushed into the inside of the pipe sleeve 25 by force applied to the proximal end side in an inserting direction of the capsule 3. Consequently, the outer shell 30 is pushed against the protrusions 25*b* and broken. The disinfection solution 31 stored on the inside of the outer shell 30 is leaked to the inside of the pipe sleeve 25 by the breakage (see FIG. 3). The insides of the pipe sleeve 25, the relay tube 26, and the treatment instrument channel 19 are disinfected by the disinfection solution 31 leaked in this way.

According to such an embodiment, the endoscope system 1 includes the capsule 3 including the outer shell 30 including the space on the inside and the disinfection solution 31 that is stored in the space of the outer shell 30 and leaked from the inside of the outer shell 30 by the breakage of the outer shell 30, and the endoscope 2 including the treatment instrument channel 19 that is provided in the insertion section 5 and causes the inside and the outside of the subject to communicate with each other and the holding section 25*a* that holds the capsule 3 on the proximal end side of the treatment instrument channel 19 on the outside of the subject. Consequently, it is possible to reduce influence of environmental bacteria on the subject.

In other words, for example, even if the endoscope 2 taken out from the sterilization package is exposed to environmental bacterial before treatment using the endoscope 2 is performed, the environmental bacteria intruding into the insides of the treatment instrument channel 19 and the like can be disinfected by the disinfection solution 31 leaked from the capsule 3. Consequently, for example, even when the treatment instrument is inserted into the subject via the treatment instrument channel 19, it is possible to prevent intrusion of the environmental bacteria into the subject. When the treatment instrument is inserted into the treatment instrument channel 19, the disinfection solution leaked into the treatment instrument channel 19 comes into contact with an outer surface of the treatment instrument. Therefore, it is possible to reduce influence on the subject by environmental bacteria adhering to the treatment instrument before the treatment instrument is inserted into the subject after sterilization.

Next, a second embodiment of the present disclosure is explained with reference to FIGS. 6 and 7. The present embodiment is different from the first embodiment explained above mainly in that a forceps plug 35 functioning as a lid body is provided in the pipe sleeve 25. Besides, the same components as the components in the first embodiment explained above are denoted by the same reference numerals and signs and explanation of the components is omitted as appropriate.

Figure 6:
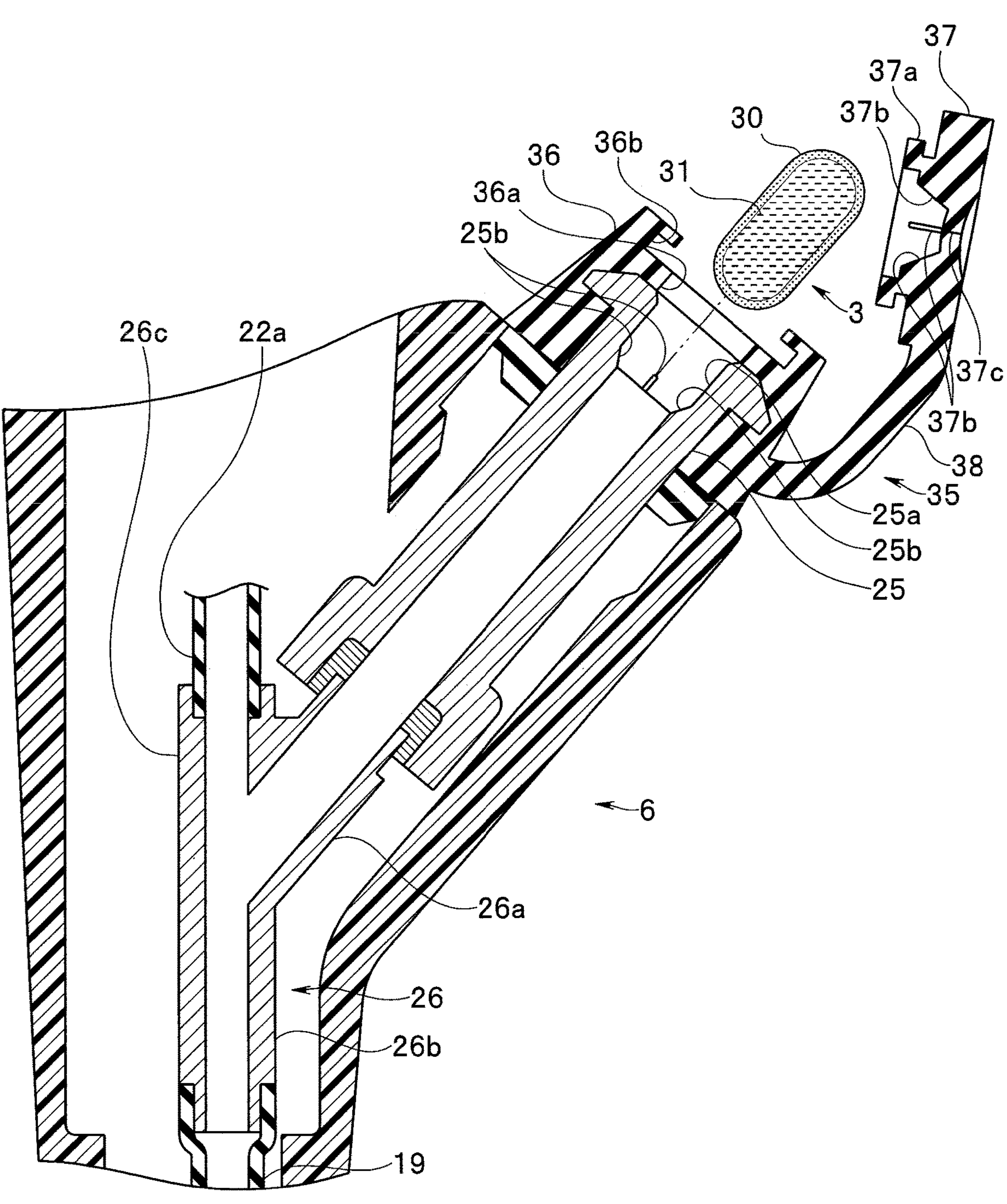
FIG. 6 relates to a second embodiment and is a main part sectional view showing the operation section and the capsule.
Figure 7:
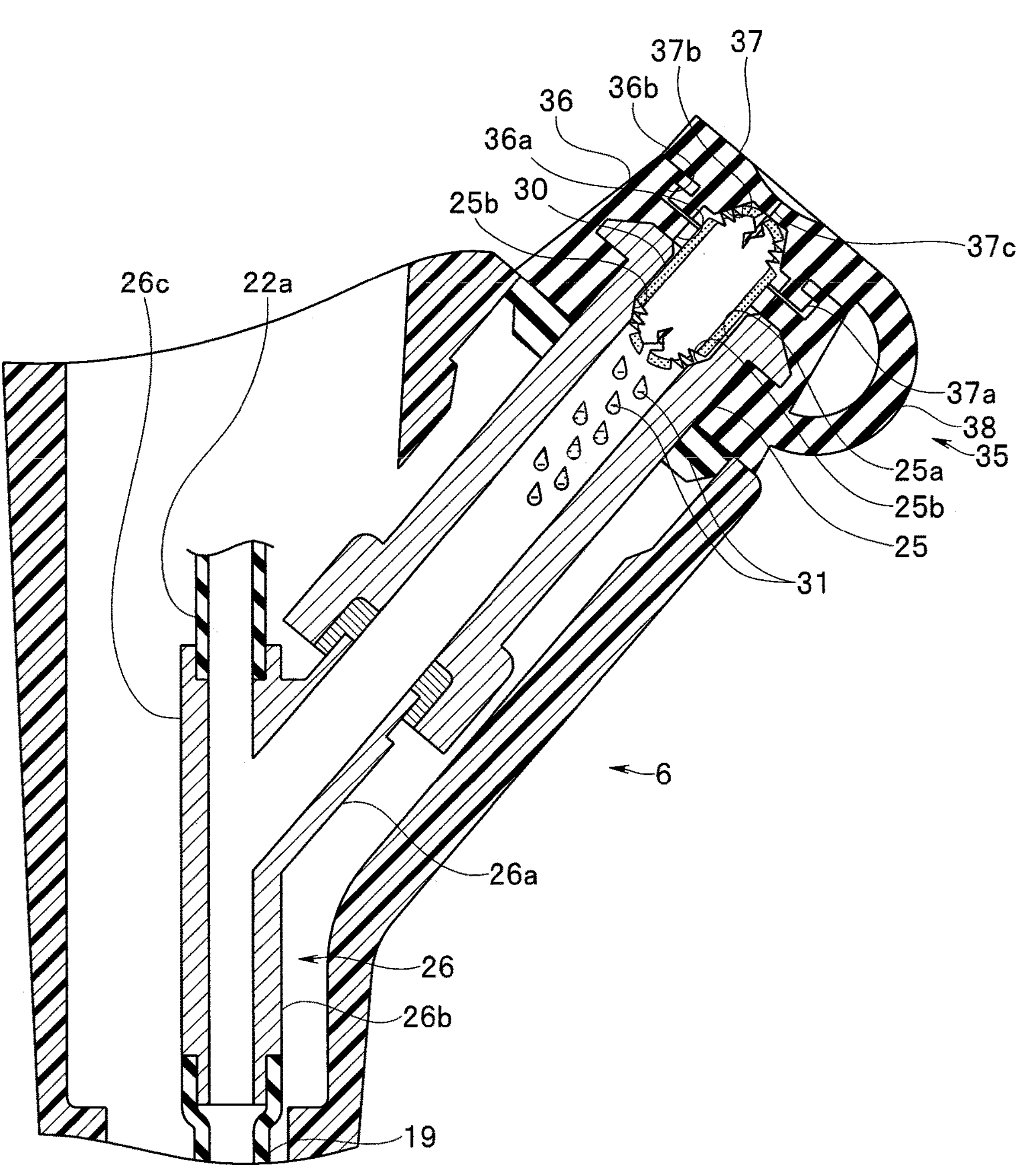
FIG. 7 relates to the second embodiment and is a main part sectional view showing the operation section and the broken capsule.

As shown in FIGS. 6 and 7, the forceps plug 35 includes a forceps plug main body 36 and a lid body 37 (lid).

The forceps plug main body 36 is configured by a member formed in a substantially cylindrical shape detachably attachable to the pipe sleeve 25. An inner circumferential surface of the forceps plug main body 36 is set as a holding section 36*a* continuous to the holding section 25*a* of the pipe sleeve 25.

A fitting recess portion 36*b* for fitting with the lid body 37 is formed on the inner circumferential surface of the forceps plug main body 36.

The lid body 37 is configured by a member formed in a substantially disk shape capable of closing an end portion of the forceps plug main body 36. In the lid body 37, a fitting projection portion 37*a* for fitting in the fitting recess portion 36*b* is provided on a contact surface side with the forceps plug main body 36.

A plurality of protrusions 37*b* are provided on an inner side of the fitting projection portion 37*a* of the lid body 37. The protrusions 37*b* are capable of coming into contact with the capsule 3 held by the holding sections 25*a* and 36*a*.

Further, a hole 37*c* for allowing the treatment instrument inserted into the treatment instrument channel 19 via the pipe sleeve 25 to pass is formed in a center of the lid body 37. The hole 37*c* is formed by, for example, a slit that pierces through the lid body 37 in a thickness direction.

Note that the forceps plug main body 36 and the lid body 37 are coupled by a coupling band 38.

In such a configuration, the capsule 3 is held by the holding sections 25*a* and 36*a* (see FIG. 6).

The capsule 3 held by the holding sections 25*a* and 36*a* is pressed by the lid body 37 when the forceps plug main body 36 is closed by the lid body 37. At that time, the protrusions 25*b* and 37*b* are pushed into the outer shell 30 of the capsule 3. The outer shell 30 is broken by the protrusions 25*b* and 37*b* and the disinfection solution 31 stored in the outer shell 30 is leaked. The insides of the pipe sleeve 25, the relay tube 26, and the treatment instrument channel 19 are disinfected by the disinfection solution 31 leaked in this way.

According to such an embodiment, the same effects as the effects in the first embodiment explained above can be achieved.

Next, a third embodiment of the present disclosure is explained with reference to FIGS. 8 to 11. The present embodiment is different from the second embodiment explained above mainly in that the capsule 3 is broken using a treatment instrument 8. Besides, the same components as the components in the second embodiment explained above are denoted by the same reference numerals and signs and explanation of the components is omitted as appropriate.

Figure 8:
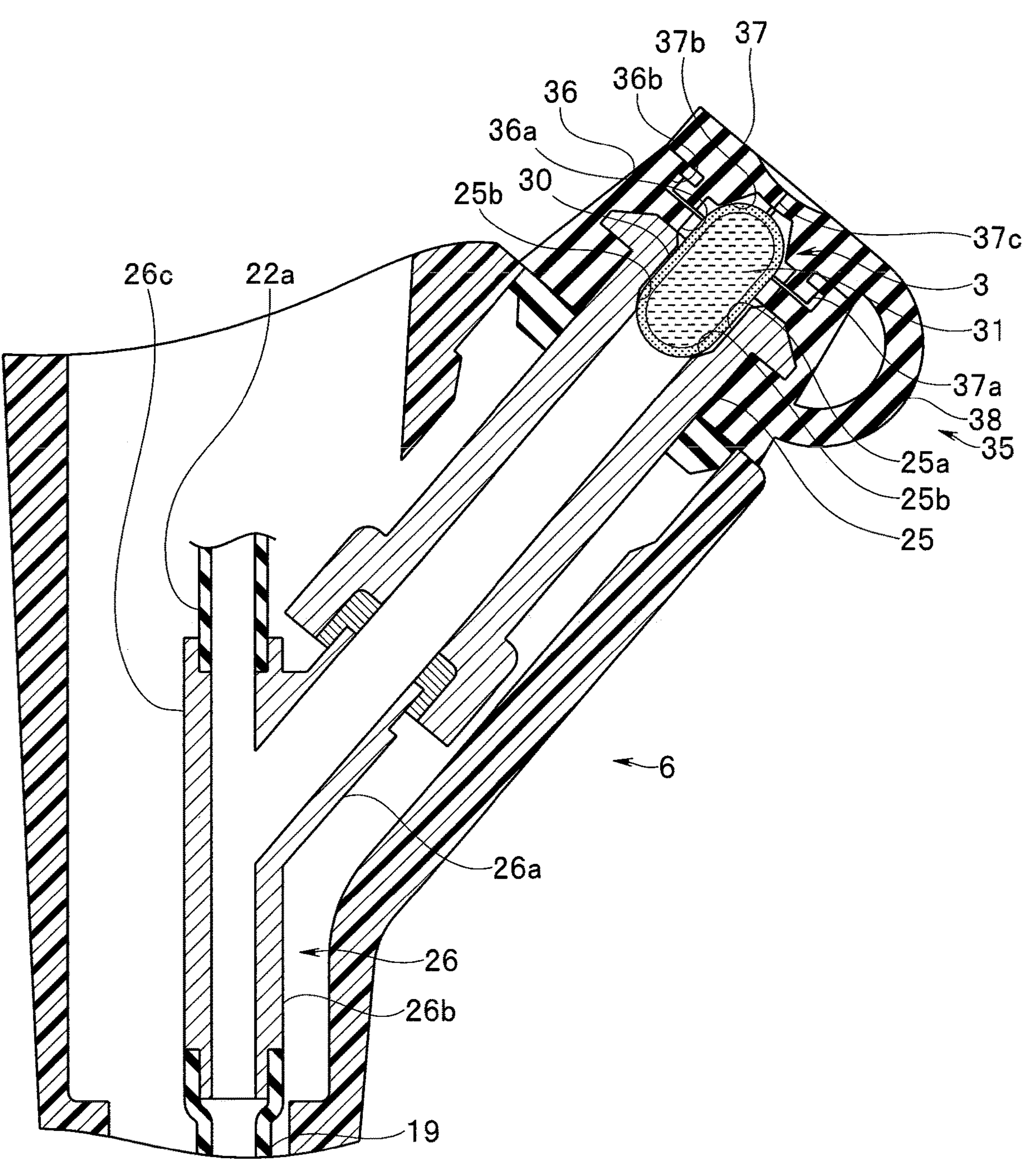
FIG. 8 relates to a third embodiment and is a main part sectional view showing the operation section and the capsule.

Here, as shown in FIG. 8, length of the capsule 3 in the present embodiment is set to, for example, length at which the capsule 3 is not broken by the protrusions 25*b* and 37*b*. In other words, the holding sections 25*a* and 36*a* are capable of holding the outer shell 30 of the capsule 3 without breaking the outer shell 30 in a state in which the lid body 37 of the forceps plug 35 is closed.

Figure 10:
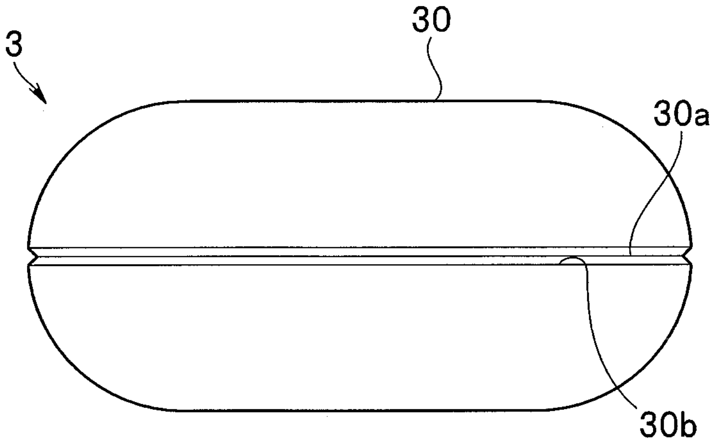
FIG. 10 relates to the third embodiment and is a side view of the capsule.

It may be desirable that, as shown in FIG. 10, a fragile section 30*a* having lower resistance to stress than other portions of the outer shell 30 is provided in the outer shell 30 of the capsule 3. In other words, the outer shell of the capsule may include a plurality of sections and a first section (the fragile section 30*a*) may have a lower resistance to stress than a second portion of the plurality of sections. For example, the thickness of the fragile section 30*a* is thinner than other areas of the outer shell 30. The fragile section 30*a* is broken faster than other areas of the outer shell 30 when pushing force is applied.

As an example, the fragile section 30*a* is formed in the longitudinal direction of the outer shell 30. To more specifically explain, a V-groove 30*b* extending in the longitudinal direction of the outer shell 30 is formed on an outer surface of the outer shell 30 in the present embodiment. A bottom of the V-groove 30*b* is set as the fragile section 30*a*. By forming the fragile section 30*a* using the V-groove 30*b* in this way, it is possible to cause a slope of the V-groove 30*b* to function as a guide surface for guiding the treatment instrument and the like toward the fragile section 30*a*.

Figure 9:
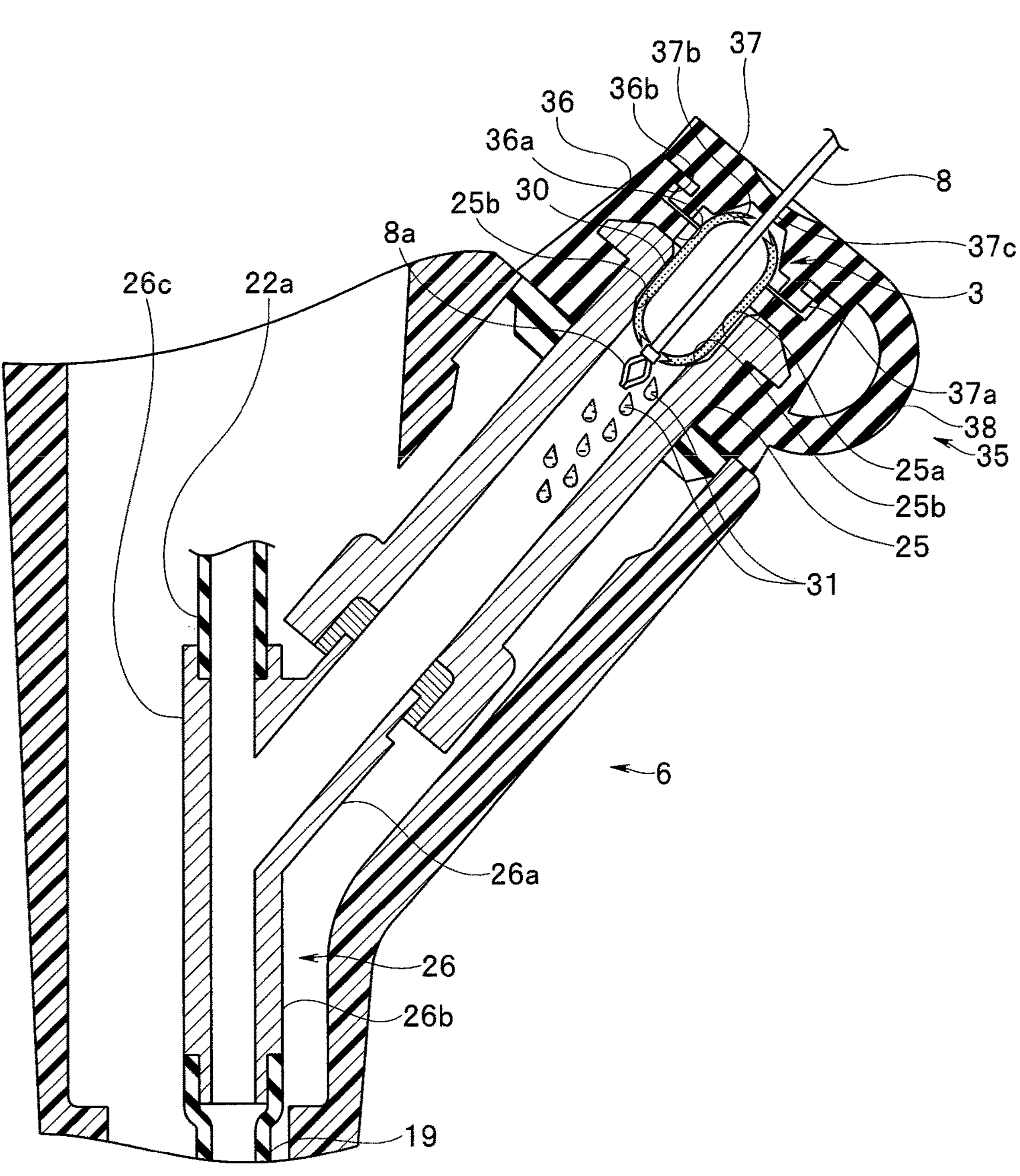
FIG. 9 relates to the third embodiment and is a main part sectional view showing the operation section and the broken capsule.

Note that, as shown in FIGS. 8 and 9, in the present embodiment, the longitudinal direction of the outer shell 30 can be defined, for example, in a relation with the pipe sleeve 25. In other words, the longitudinal direction of the outer shell 30 is a direction in which the capsule 3 is inserted into the pipe sleeve 25 and is a direction in which the treatment instrument 8 is inserted into the pipe sleeve 25.

Figure 11:
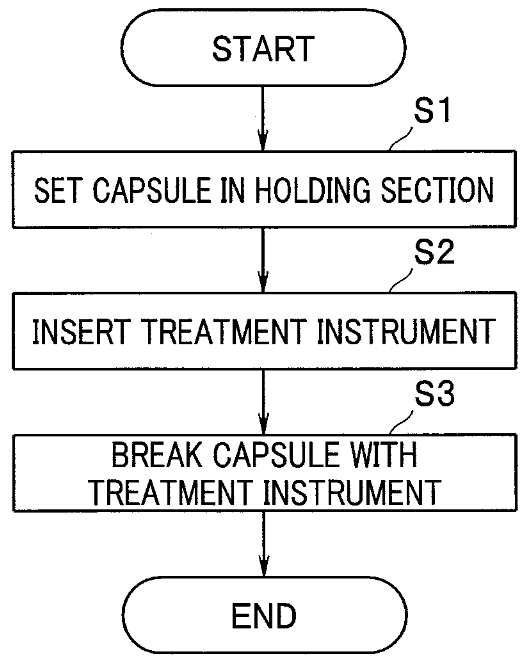
FIG. 11 relates to the third embodiment and is a flowchart showing a disinfection method for an endoscope.

Next, a disinfection method for the endoscope system 1 configured in this way is explained according to a flowchart shown in FIG. 11.

After taking out the endoscope 2 from a sterilization package, for example, as shown in FIG. 8, a surgeon or the like sets the capsule 3 in the holding sections 25*a* and 36*a* (step S1). In other words, after inserting the capsule 3 into insides of the holding sections 25*a* and 36*a*, the surgeon or the like closes the forceps plug main body 36 of the forceps plug 35 with the lid body 37. Note that, in the present embodiment, it is possible to insert the insertion section 5 into a subject in a state in which the capsule 3 is kept set in this way.

Next, the surgeon or the like inserts the treatment instrument 8 into the inside of the pipe sleeve 25 via the hole 37*c* provided in the lid body 37 (step S2).

The surgeon or the like pushes the treatment instrument 8 into the inside of the pipe sleeve 25 to thereby break the outer shell 30 of the capsule 3 (step S3). In other words, the treatment instrument 8 is pushed into the inside of the pipe sleeve 25, whereby an end effector 8*a* provided at a distal end of the treatment instrument 8 is pressed against the fragile section 30*a* while being guided by the V-groove 30*b*. The outer shell 30 is broken along the fragile section 30*a* by the end effector 8*a* pressed against the fragile section 30*a*.

According to such an embodiment, in addition to the effects obtained in the respective embodiments explained above, it is possible to perform disinfection of the treatment instrument channel 19 and the like at timing immediately before the treatment instrument 8 is used.

Further, the treatment instrument 8 that breaks the outer shell 30 of the capsule 3 is disinfected by the disinfection solution when passing the internal space of the outer shell 30. Therefore, it is possible to simultaneously realize disinfection for not only the treatment instrument channel 19 and the like but also the treatment instrument 8.

Here, it is possible to adopt various shapes as a shape of the outer shell 30 of the capsule 3.

Figure 12:
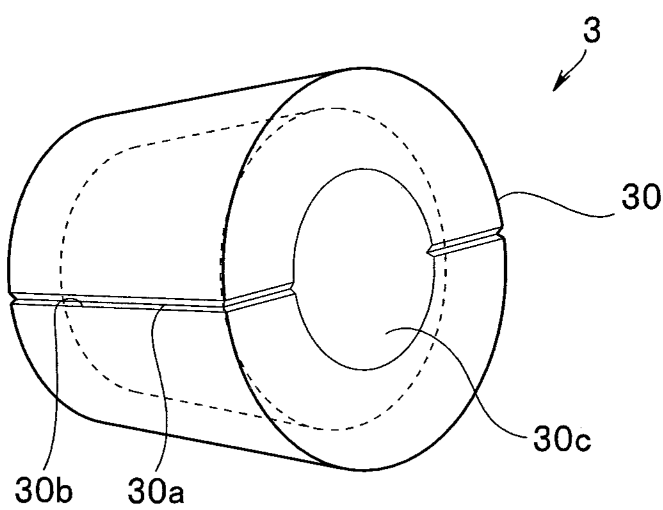
FIG. 12 relates to a first modification of the third embodiment and is a perspective view of the capsule.
Figure 13:
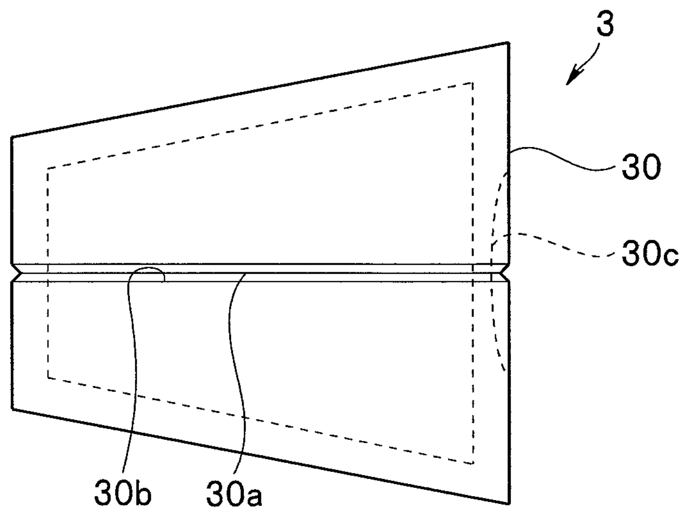
FIG. 13 relates to the first modification of the third embodiment and is a side view of the capsule.

For example, as shown in FIGS. 12 and 13, it is possible to form the outer shell 30 in a substantially truncated cone shape. Note that, as an outer diameter of the outer shell 30 shown in FIGS. 12 and 13, an outer diameter on one end side (the distal end side) is set smaller than the inner diameter r2 of the pipe sleeve 25 (and the inner diameter of the treatment instrument channel 19) and an inner diameter on the other end side (the proximal end side) is set larger than the inner diameter r2 of the pipe sleeve 25.

Further, a recess portion 30*c* is provided in a surface on the proximal end side (a large diameter side) of the outer shell 30. A part of a ridgeline of the recess portion 30*c* is connected to the fragile section 30*a*.

Figure 14:
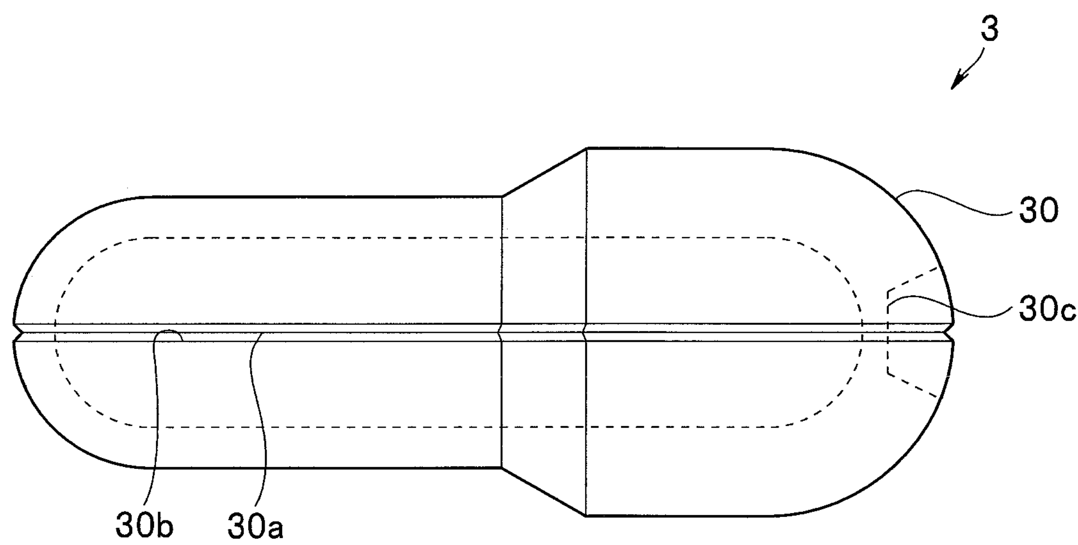
FIG. 14 relates to a second modification of the third embodiment and is a side view of the capsule.

For example, as shown in FIG. 14, it is also possible to form the outer shell 30 in a shape obtained by combining two substantially long spherical shapes having different outer diameters.

Figure 15:
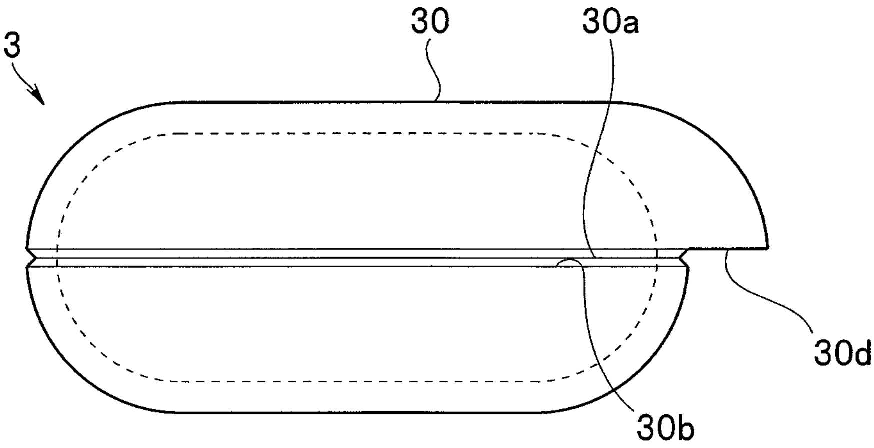
FIG. 15 relates to a third modification of the third embodiment and is a side view of the capsule.

Further, for example, as shown in FIG. 15, it is also possible to provide, at an end portion in the longitudinal direction of the outer shell 30, a protrusion 30*d* for guiding the treatment instrument 8 and the like to the fragile section 30*a*.

Next, a fourth embodiment of the present disclosure is explained with reference to FIG. 16 to FIG. 19. The present embodiment is different from the second embodiment explained above mainly in that the capsule 3 is set in the holding sections 25*a* and 36*a* in a state in which the capsule 3 is held by the lid body 37. Besides, the same components as the components in the second embodiment explained above are denoted by the same reference numerals and signs and explanation of the components is omitted as appropriate.

Figure 16:
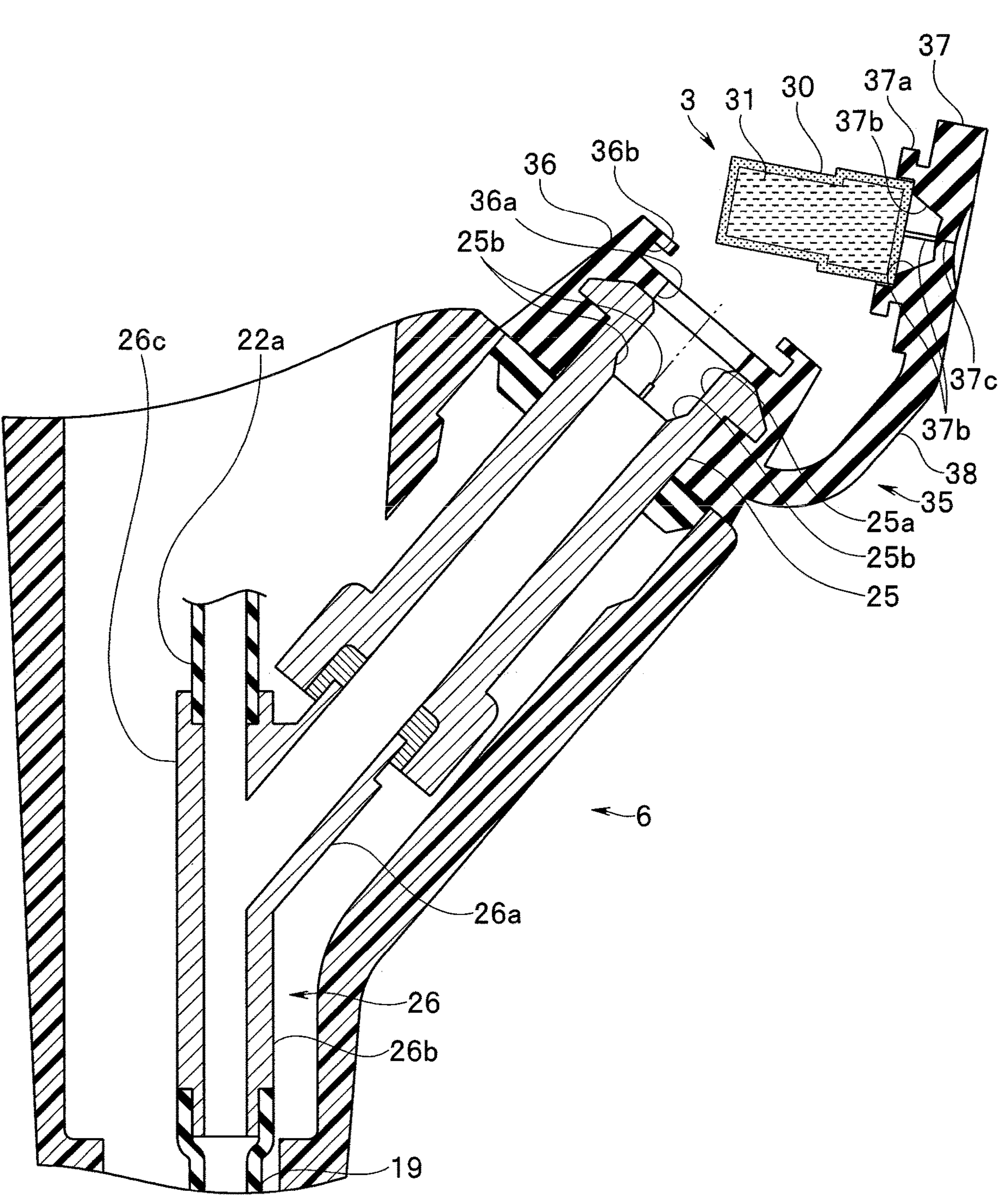
FIG. 16 relates to a fourth embodiment and is a main part sectional view showing the operation section and the capsule.
Figure 17:
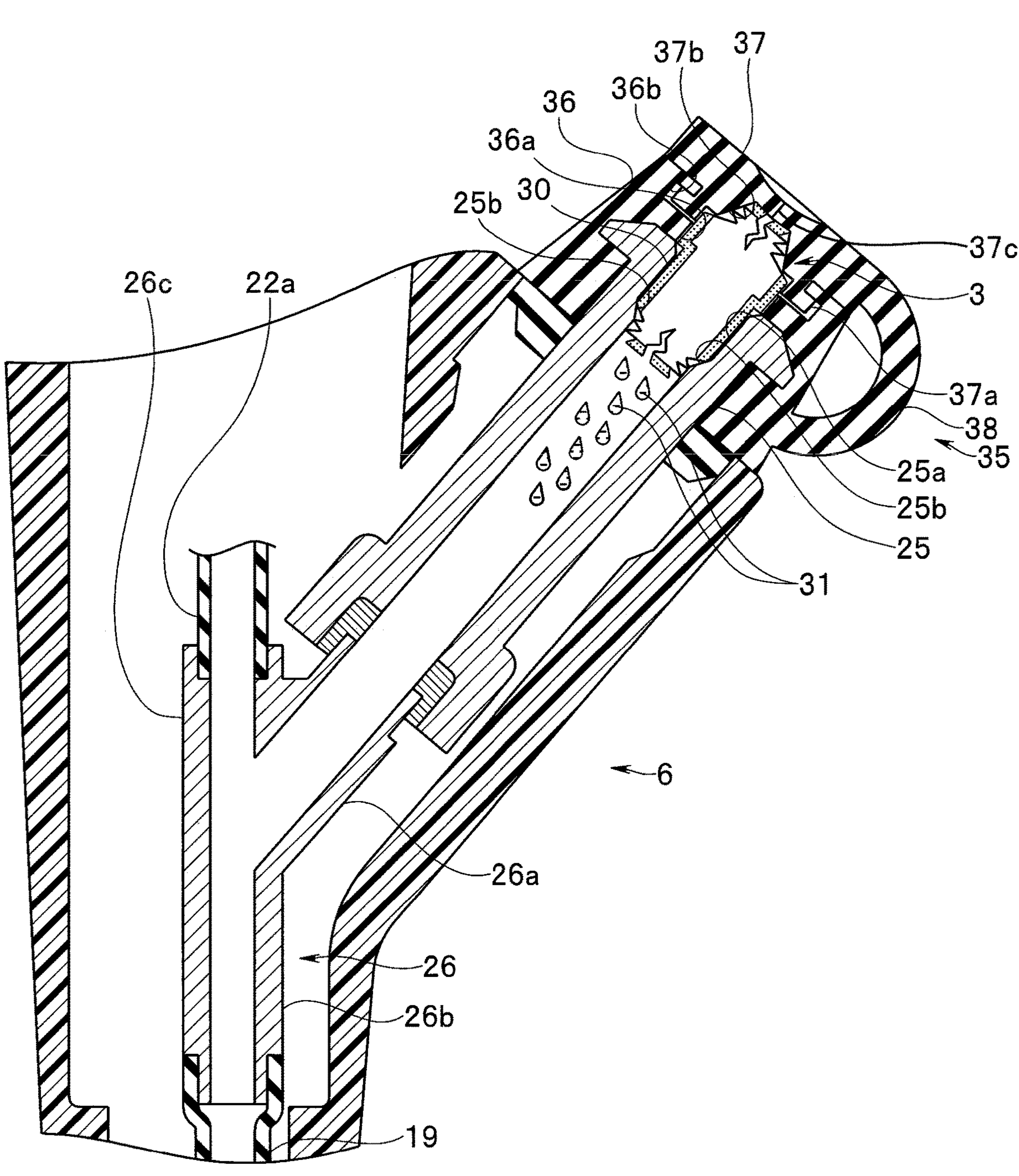
FIG. 17 relates to the fourth embodiment and is a main part sectional view showing the operation section and the broken capsule.
Figure 18:
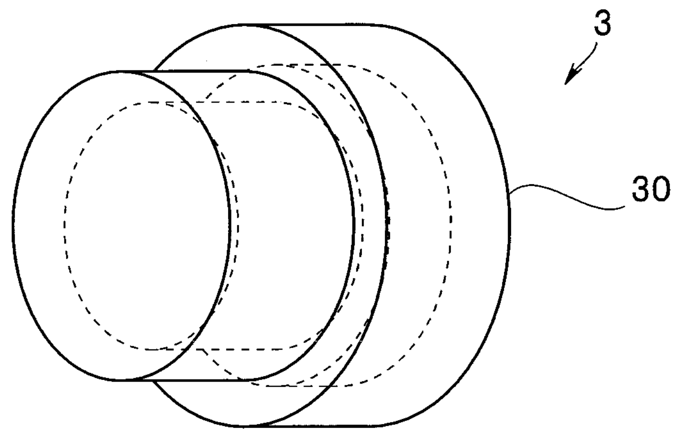
FIG. 18 relates to the fourth embodiment and is a perspective view showing the capsule from a distal end side.
Figure 19:
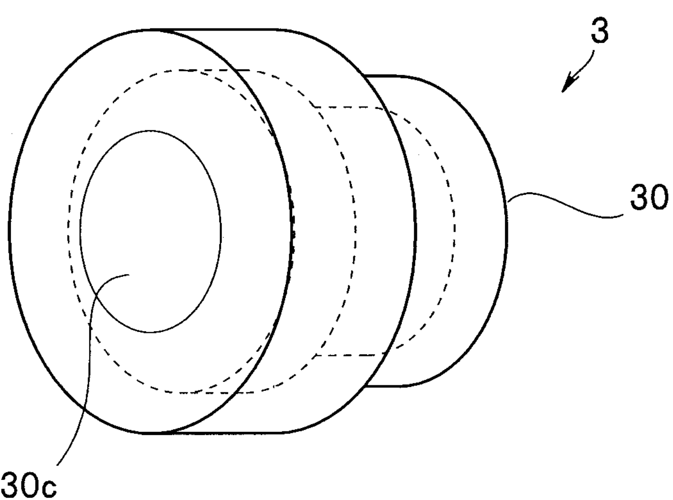
FIG. 19 relates to the fourth embodiment and is a perspective view showing the capsule from a proximal end side.

For example, as shown in FIGS. 16, 18, and 19, the outer shell 30 of the capsule 3 in the present embodiment is formed in a multistage columnar shape obtained by combining two columns having different outer diameters.

A columnar section having a large diameter formed on the proximal end side in the longitudinal direction of the outer shell 30 has an outer diameter that can fit in an inner circumference of the fitting projection portion 37*a* of the lid body 37.

On the other hand, a columnar section having a small diameter formed on the distal end side in the longitudinal direction of the outer shell 30 has an outer diameter that can be inserted into the holding sections 25*a* and 36*a*.

The proximal end side of the capsule 3 in which the outer shell 30 is formed in this way is set in the fitting projection portion 37*a* of the lid body 37 (see FIG. 16).

The distal end side of the capsule 3 is inserted into the insides of the holding sections 25*a* and 36*a* when the lid body 37 closes the forceps plug main body 36. When the fitting projection portion 37*a* of the lid body 37 is fitted in the fitting recess portion 36*b* of the forceps plug main body 36, the outer shell 30 of the capsule 3 is broken by being pressed against the protrusions 25*b* and 37*b* (see FIG. 17).

According to such an embodiment, it is possible to achieve the same effects as the effects in the second embodiment explained above.

Next, a fifth embodiment of the present disclosure is explained with reference to FIGS. 20 and 21. The present embodiment is different from the first embodiment explained above mainly in that a film 40 is provided at a distal end (the distal end portion 10) of the insertion section 5 of the endoscope 2 shown in the first embodiment explained above. Besides, the same components as the components in the first embodiment explained above are denoted by the same reference numerals and signs and explanation of the components is omitted as appropriate.

Figure 20:
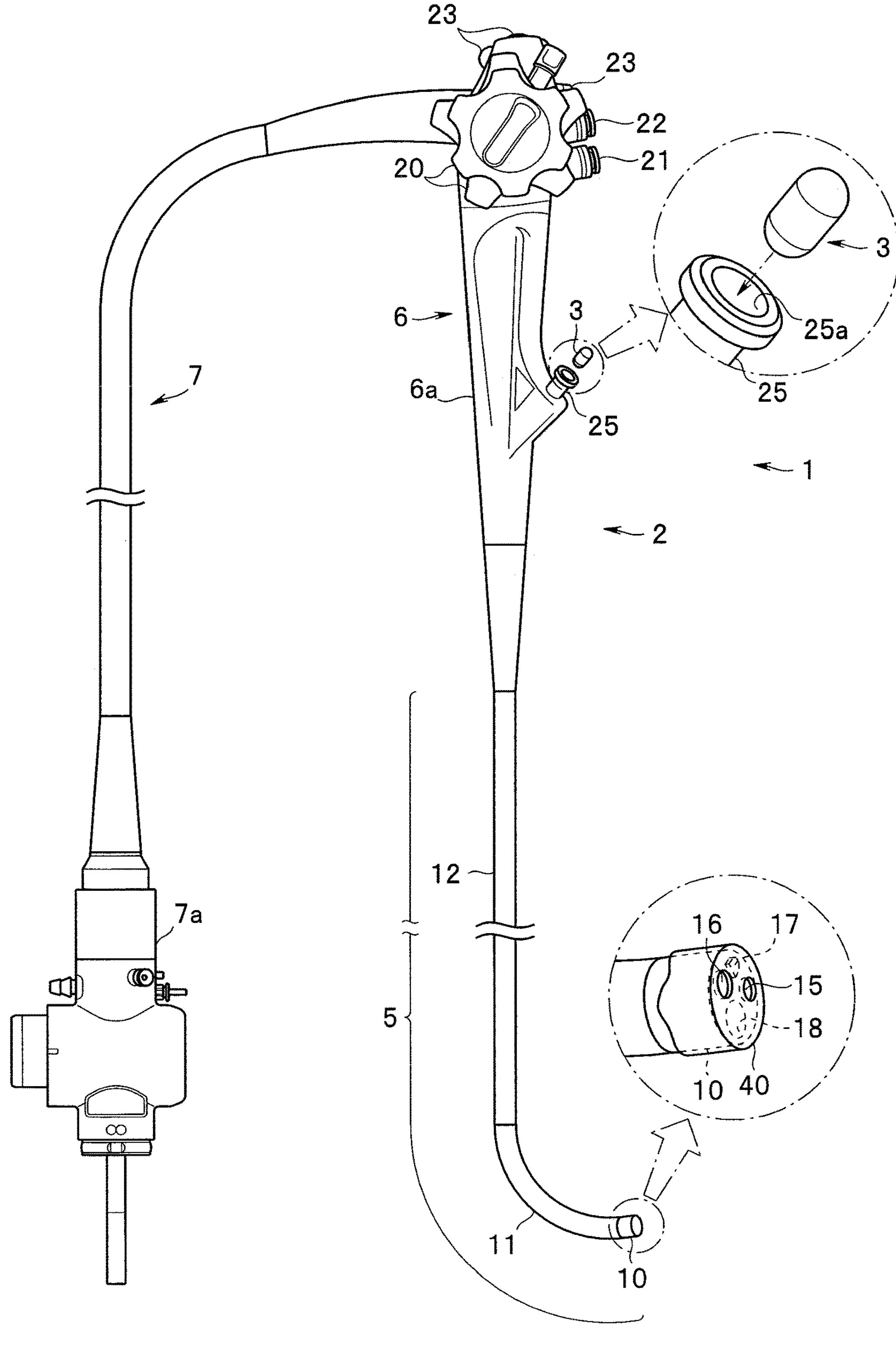
FIG. 20 relates to a fifth embodiment and is a schematic configuration diagram of an endoscope system.
Figure 21:
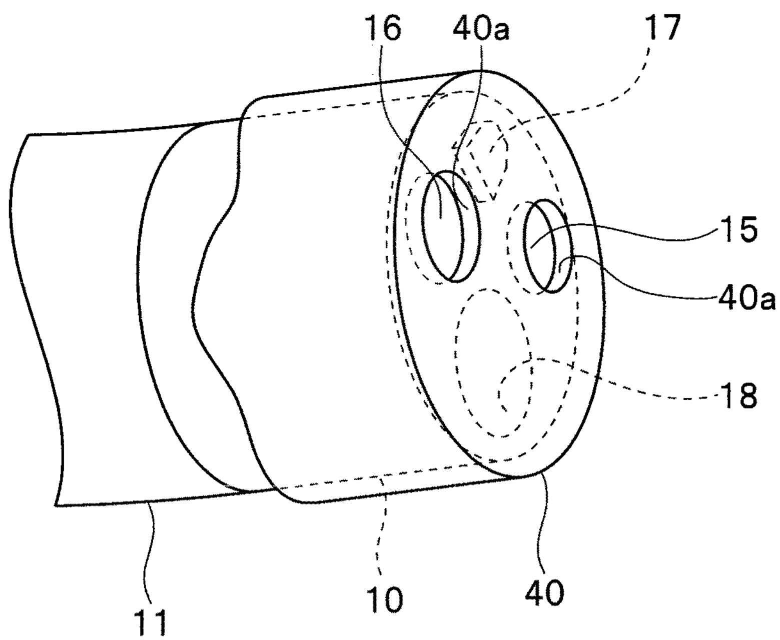
FIG. 21 relates to the fifth embodiment and is a perspective view showing a distal end portion of the endoscope.

As shown in FIGS. 20 and 21, a meltable film 40 is provided at the distal end portion 10. The film 40 covers at least the distal end side opening 18. In the present embodiment, the film 40 is provided to cover a distal end face and a side surface of the distal end portion 10.

However, in order to secure visibility at the time when the insertion section 5 is inserted into an inside of the subject, the illumination window and the observation window provided at the distal end portion 10 are excluded from covering targets by the film 40. In other words, in the film 40, an opening 40*a* for opening the illumination window and the observation window is formed.

Here, the film 40 is formed by, for example, wafer paper. Strength of the film 40 is set higher than strength of the outer shell 30 of the capsule 3. The setting of the strength can be realized by adjusting, for example, a film thickness of the film 40.

With such a configuration, even if the outer shell 30 of the capsule 3 held by the holding section 25*a* is deformed without being broken and the capsule 3 intrudes into the inside of the treatment instrument channel 19, it is possible to accurately break the outer shell 30.

In other words, by covering the distal end side opening 18 with the film 40 having the higher strength than the outer shell 30, it is possible to break the capsule 3 intruding into the inside of the treatment instrument channel 19 with the treatment instrument 8 inserted into the treatment instrument channel 19 without discharging the capsule 3 from the distal end side opening 18.

In the present embodiment, before holding the capsule 3 in the holding section 25*a*, it is also possible to insert another capsule 3 having an outer diameter smaller than the inner diameter of the treatment instrument channel 19 into the inside of the treatment instrument channel 19 via the pipe sleeve 25. The outer shell 30 of the capsule 3 inserted into the inside of the treatment instrument channel 19 in this way can be broken by the film 40 covering the distal end side opening 18 and the treatment instrument 8 inserted into the treatment instrument channel 19. Consequently, it is possible to perform disinfection for the distal end side of the treatment instrument channel 19 separately from the proximal end side.

In addition, by covering the distal end side opening 18 with the film 40, it is also possible to prevent environmental bacteria from intruding into the inside of the treatment instrument channel 19 from the distal end side opening 18.

Note that, since the film 40 is melted by, for example, body fluid of the subject after the insertion section 5 is inserted into the inside of the subject, the film 40 does not affect various treatments performed using the endoscope 2.

Note that the present disclosure is not limited to the respective embodiments explained above. Various modifications and changes of the present disclosure are possible. The modifications and the changes are also within a technical scope of the present disclosure. For example, it goes without saying that the configurations of the respective embodiments and the respective modifications explained above may be combined as appropriate.

Here, in the respective embodiments explained above, the configuration in which the disinfection of the treatment instrument channel 19 and the like is performed using the capsule 3 is explained. However, it is also possible to perform the disinfection of the treatment instrument channel 19 and the like using the treatment instrument 8.

Figure 22:
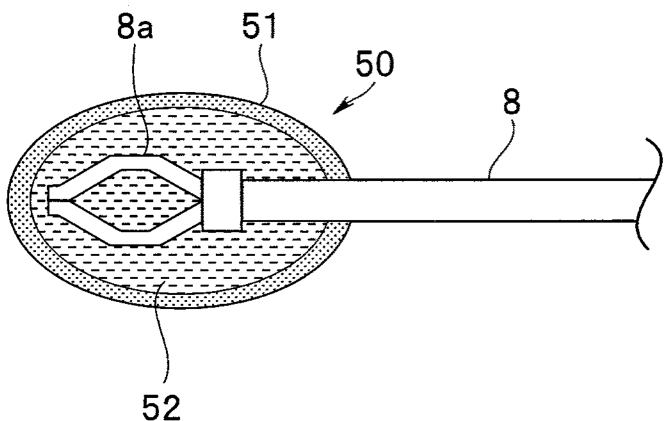
FIG. 22 relates to a first disclosure example and is an explanatory diagram showing a distal end side of a treatment instrument.
Figure 23:
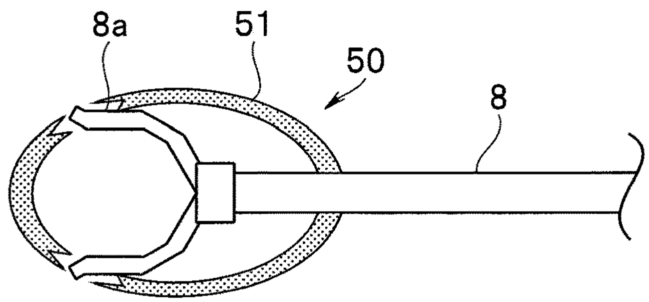
FIG. 23 relates to the first disclosure example and is an explanatory diagram showing the distal end side of the treatment instrument with the capsule broken.

For example, as shown in FIGS. 22 and 23, it is also possible to provide a capsule 50 around the end effector 8*a* of the treatment instrument 8. The capsule 50 includes an outer shell 51 and a disinfection solution 52.

After the treatment instrument 8 is inserted into the inside of the treatment instrument channel 19, the outer shell 51 of the capsule 50 is broken by, for example, causing the end effector 8*a* to operate as shown in FIG. 23. Consequently, it is possible to perform disinfection of the treatment instrument channel 19 and the like.

Figure 24:
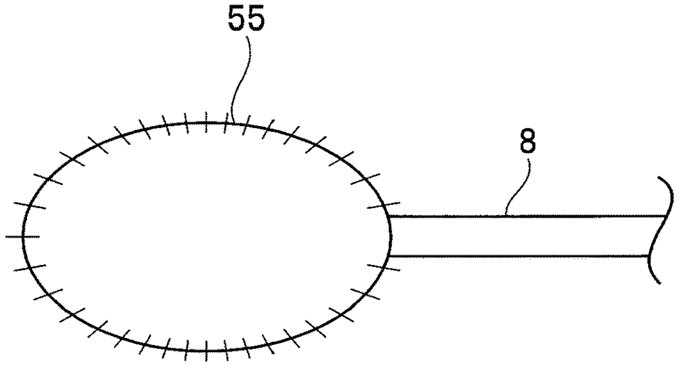
FIG. 24 relates to a second disclosure example and is an explanatory diagram showing the distal end side of the treatment instrument.

For example, as shown in FIG. 24, it is also possible to attach cotton 55 impregnated with a disinfection solution to the distal end of the treatment instrument 8 and disinfect the treatment instrument channel 19 and the like.

Figure 25:
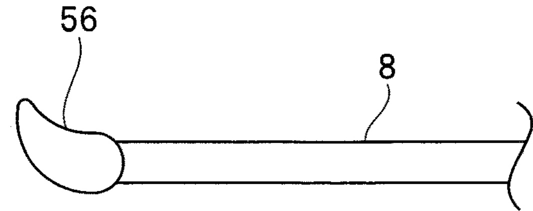
FIG. 25 relates to a third disclosure example and is a perspective view showing the distal end side of the treatment instrument.

For example, as shown in FIG. 25, it is also possible to attach a swab 56 impregnated with a disinfection solution to the distal end of the treatment instrument 8 and disinfect a forceps raising base (forceps elevator) (not shown) and the like.

In the embodiments explained above, the endoscope 1 is mainly conceivable as medical insertion equipment. However, the medical insertion equipment may be a catheter, an over tube attached with a conduit, or the like including a treatment instrument channel and used for insertion of a treatment instrument.

The endoscope 2 is the single-use endoscope that is discarded after being used once as explained above. However, the endoscope 1 may be a reuse-type endoscope that is repeatedly used or the endoscope 1 may be used to more surely reduce influence of environmental bacteria on a subject until the endoscope 1 is inserted into the subject after sterilization treatment and treatment is performed.

1. A medical insertion equipment system comprising:
   at least one capsule including an outer shell including a space on an inside, and a disinfectant that is stored in the space in the outer shell and leaked from the inside of the outer shell by breakage of the outer shell; and
   insertion equipment including an insertion section that is inserted into an inside of a subject, a conduit provided in the insertion section and configured to cause the inside and an outside of the subject to communicate with each other, and a holding section configured to hold the capsule in the conduit.
2. The medical insertion equipment system according to example 1, wherein the holding section is configured to hold the capsule on an end portion side of the conduit on the outside of the subject.
3. The medical insertion equipment system according to example 1, further comprising a pipe sleeve connected to the end portion side of the conduit on the outside of the subject, wherein
   the holding section is provided in the pipe sleeve.
4. The medical insertion equipment system according to example 3, wherein the pipe sleeve includes, on an inner surface, a protrusion that comes into contact with an outer surface of the capsule.
5. The medical insertion equipment system according to example 3, further comprising a lid body attached to the pipe sleeve, wherein
   the holding section is provided on the inner surface of the pipe sleeve and in the lid body.
6. The medical insertion equipment system according to example 5, wherein the lid body is a forceps plug including a hole for allowing a treatment instrument inserted into the conduit to pass.
7. The medical insertion equipment system according to example 1, wherein
   the outer shell includes a fragile section having lower resistance to stress than other portions of the outer shell, and
   the fragile section is broken by force from an outside applied in a direction in which the capsule is inserted into an inside of the conduit.
8. The medical insertion equipment system according to example 7, wherein the fragile section is broken by stress applied to an end portion in the direction in which the capsule is inserted into the conduit.

9. The medical insertion equipment system according to example 8, wherein the fragile section includes, on an inner surface or an outer surface of the outer shell, a groove extending in the direction in which the capsule is inserted into the conduit.

10. The medical insertion equipment system according to example 8, wherein the outer shell of the capsule includes, at an end portion in the direction in which the capsule is inserted into the inside of the conduit, a groove including a slope for guiding an appliance inserted into the conduit toward the fragile section.

11. The medical insertion equipment system according to example 7, wherein the outer shell of the capsule includes a recess portion on a surface, and a ridgeline of the recess portion is connected to the fragile section.

12. The medical insertion equipment system according to example 1, wherein the outer shell of the capsule is formed in a truncated cone shape, an outer diameter on one end side of the capsule is smaller than an inner diameter of the conduit and an outer diameter on another end side of the capsule is larger than the inner diameter of the conduit.

13. The medical insertion equipment system according to example 1, wherein an outer diameter of the outer shell of the capsule is larger than an inner diameter of the conduit further on a distal end side than the holding section and smaller than an inner diameter of the holding section.

14. The medical insertion equipment system according to example 1, wherein the outer shell of the capsule is formed to contain a material that is melted by at least one of body fluid or body temperature of a living body.

15. The medical insertion equipment system according to example 1, wherein a meltable film that covers an opening section of the conduit is provided at a distal end portion of the insertion section of the insertion equipment.

16. The medical insertion equipment system according to example 15, wherein the distal end portion includes an illumination window and an observation window, and the film covers a portion excluding the illumination window and the observation window.

17. The medical insertion equipment system according to example 15, wherein strength of the film is higher than strength of the outer shell of the capsule.

18. The medical insertion equipment system according to example 1, wherein the at least one capsule includes a plurality of capsules, the plurality of capsules being inserted into the holding section or the conduit of the insertion equipment.

19. A capsule comprising:

an outer shell including a space on an inside; and a disinfectant that is stored in the space in the outer shell and leaked from the inside of the outer shell by breakage of the outer shell, the capsule being inserted into a conduit of medical insertion equipment including an insertion section that is inserted into an inside of a subject and the conduit provided in the insertion section and configured to cause the inside and an outside of the subject to communicate with each other.

20. A medical insertion equipment disinfection method comprising:

holding, on an end portion side of a conduit of insertion equipment on an outside of a subject, the insertion equipment including an insertion section that is inserted into an inside of the subject and a conduit provided in the insertion section and configured to cause the inside and the outside of the subject to communicate with each other, a capsule including an outer shell including a space on an inside and a disinfectant stored in the space in the outer shell;

inserting a treatment instrument from an end portion side of the conduit on the outside of the subject; and breaking the outer shell of the capsule with the treatment instrument inserted into the conduit to leak the disinfectant to an inside of the conduit.

What is claimed is:

1. A medical insertion equipment system, comprising:

a capsule including an outer shell and an interior space;

a disinfectant located in the interior space of the capsule; and a medical insertion instrument including:

an operation section, an insertion section configured for insertion into a subject, an insertion conduit located in the insertion section, and a fixture located in the operation section, the fixture including a body having a receiver space for holding at least a portion of the capsule, wherein the insertion conduit extends along an insertion axis from a distal end side of the insertion section to a proximal end side of the insertion section, wherein the fixture includes an opening in a surface of the receiver space, wherein the opening is in fluid communication with the insertion conduit via a connecting conduit, wherein the receiver space in the body of the fixture is a first portion receiver space, wherein the fixture further includes a lid, wherein the lid includes a second portion receiver space, wherein the lid is attached to the fixture for movement between an open position and a closed position, wherein, in the closed position, the lid contacts the body of the fixture to form a closed receiver space, the closed receiver space including the first portion receiver space and the second portion receiver space, wherein a surface of the first portion receiver space includes a first protrusion, and wherein, when the capsule is in the closed receiver space, the first protrusion pierces the outer shell of the capsule.

2. A medical insertion equipment system, comprising:

a capsule including an outer shell and an interior space;

a disinfectant located in the interior space of the capsule; and a medical insertion instrument including:

an operation section, an insertion section configured for insertion into a subject, an insertion conduit located in the insertion section, and a fixture located in the operation section, the fixture including a body having a receiver space for holding at least a portion of the capsule, wherein the insertion conduit extends along an insertion axis from a distal end side of the insertion section to a proximal end side of the insertion section, wherein the fixture includes an opening in a surface of the receiver space, wherein the opening is in fluid communication with the insertion conduit via a connecting conduit, wherein the receiver space in the body of the fixture is a first portion receiver space, wherein the fixture further includes a lid, wherein the lid includes a second portion receiver space, wherein the lid is attached to the fixture for movement between an open position and a closed position, wherein, in the closed position, the lid contacts the body of the fixture to form a closed receiver space, the closed receiver space including the first portion receiver space and the second portion receiver space, wherein a surface of the second portion receiver space includes a protrusion, and wherein, when the capsule is in the closed receiver space, the protrusion pierces the outer shell of the capsule.

3. The medical insertion equipment system according to claim 2, wherein a surface of the first portion receiver space includes a first protrusion, and wherein, when the capsule is in the closed receiver space, the first protrusion pierces the outer shell of the capsule.

4. The medical insertion equipment system according to claim 1, wherein a surface of the second portion receiver space includes a second protrusion, and wherein, when the capsule is in the closed receiver space, the second protrusion pierces the outer shell of the capsule.

5. The medical insertion equipment system according to claim 2, wherein the lid is a forceps plug including a hole for receiving a treatment instrument to be inserted into the insertion conduit.

6. The medical insertion equipment system according to claim 1, wherein the outer shell of the capsule includes a plurality of sections, wherein a first section of the plurality of sections has a lower resistance to stress than a second portion of the plurality of sections.

7. The medical insertion equipment system according to claim 6, wherein the at least portion of the capsule is positioned into the receiver space by movement in an insertion direction, and wherein, with the at least portion of the capsule located in the receiver space, a force in the insertion direction breaks the first section of the plurality of sections.

8. The medical insertion equipment system according to claim 6, wherein a force in the insertion direction is applied to an end portion of the capsule.

9. The medical insertion equipment system according to claim 6, wherein the first section of the plurality of sections includes a groove extending in the insertion direction, and wherein the groove is on an inner surface or an outer surface of the outer shell.

10. The medical insertion equipment system according to claim 6, wherein the outer shell of the capsule includes a groove, wherein the groove is located, relative to the insertion direction, at an end portion of the capsule, and wherein the groove includes a sloping surface to guide an appliance inserted into the receiver space toward the first section of the plurality of sections.

11. The medical insertion equipment system according to claim 1, wherein the outer shell of the capsule has a shape of a truncated cone including a first end surface, a second end surface, and a side surface connecting the first end surface to the second end surface, wherein an outer diameter of the first end surface is smaller than a diameter of the opening in the surface of the receiver space, wherein the outer diameter of the first end surface is smaller than an inner diameter of the connecting conduit, wherein an outer diameter of the second end surface is larger than diameter of the opening in the surface of the receiver space, and wherein an outer diameter of the second end surface is larger than the inner diameter of the connecting conduit.

12. The medical insertion equipment system according to claim 1, wherein a first portion of the outer shell of the capsule has a shape of a first cylinder, wherein a second portion of the outer shell of the capsule has a shape of a second cylinder, wherein an outer diameter of the second cylinder is larger than an outer diameter of the first cylinder, and wherein the outer diameter of the first cylinder is smaller than a diameter of the opening in the surface of the receiver space and is smaller than an inner diameter of the connecting conduit.

13. The medical insertion equipment system according to claim 11, wherein a height of a first cylinder is larger than a length of a side surface of the receiver space.

14. The medical insertion equipment system according to claim 11, wherein a first end of a first cylinder is a distal end of the capsule and a first end of a second cylinder is a second end of the capsule, and wherein at least on of (a) an end surface at the first end of the first cylinder has a curved shape and (b) an end surface at the second end of the first cylinder has a curved shape.

15. The medical insertion equipment system according to claim 1, wherein the distal end side of the insertion section includes a film covering an opening of the insertion conduit, and wherein the capsule is formed of a material that (i) has a melting temperature less than 38° C. or (ii) is dissolvable by contact with a body fluid.

16. The medical insertion equipment system according to claim 15, wherein the distal end side of the insertion section includes an illumination window and an observation window, and wherein the film does not cover the illumination window and does not cover the observation window.

17. The medical insertion equipment system according to claim 15, wherein a strength of the film is higher than a strength of the outer shell of the capsule.

18. The medical insertion equipment system according to claim 1, wherein the lid is a forceps plug including a hole for receiving a treatment instrument to be inserted into the insertion conduit.

* * * * *